United States Patent [19]

Schachar

[11] Patent Number: 4,622,967

[45] Date of Patent: Nov. 18, 1986

[54] AURICULAR INSTRUMENT

[76] Inventor: Ronald A. Schachar, P.O. Box 124, Denison, Tex. 75020

[21] Appl. No.: 650,118

[22] Filed: Sep. 13, 1984

[51] Int. Cl.⁴ .............................................. A61B 17/36
[52] U.S. Cl. ................................... 128/303.15; 128/9
[58] Field of Search ........................ 128/6, 8, 9, 303.1, 128/395, 303.15

[56] References Cited

U.S. PATENT DOCUMENTS

| | | | |
|---|---|---|---|
| 3,020,912 | 2/1962 | Chester | 128/9 |
| 3,605,730 | 9/1971 | Hotchkiss | 128/9 |
| 3,858,577 | 1/1975 | Bass et al. | 128/8 |
| 3,978,850 | 9/1976 | Moore et al. | 128/9 |
| 4,207,874 | 6/1980 | Chox | 128/6 |
| 4,309,998 | 1/1982 | Rosa et al. | 128/303.1 |
| 4,396,285 | 8/1983 | Presta et al. | 128/303.1 |
| 4,408,602 | 10/1983 | Nakajima | 128/303.1 |
| 4,418,689 | 12/1983 | Kanazawa | 128/6 |
| 4,434,800 | 3/1984 | Anson et al. | 128/9 |
| 4,454,882 | 6/1984 | Takano | 128/6 |
| 4,503,854 | 3/1985 | Jako | 128/303.1 |
| 4,566,439 | 1/1986 | Burgin | 128/6 |

Primary Examiner—Paul J. Hirsch
Attorney, Agent, or Firm—Jerry W. Mills; Gregory M. Howison

[57] ABSTRACT

An auricular instrument (10) for the therapy of otitis media has a Q-switched laser (26) whose "giant pulse" output is especially suitable for forming a clean, round hole in a patient's tympanic membrane for draining the afflicted middle ear. The Q-switched laser (26) uses a neodymium YAG (yttrium-aluminum-garnet) lasing medium and its output is non-visible to the human eye. A gas laser (32) using a helium-neon lasing medium provides a low power, continuous beam of visible light upon which the output of the Q-switched laser (26) is made to ride by suitable optics. Both radiations emerge from the ear probe of a conically-tapering ear probe-/cylindrical eyepiece (12) combination similar to that comonly found in otoscopes. With the probe being inserted in the patient's outer ear and with the eyepiece being looked through by a physician controlling the Q-switched laser (26), the physician will see a localized membrane area illuminated by the gas laser (32) and, as he controls the shots fired by the Q-switched laser (26), he will observe the progressive formation of the hole centrally of the localized area.

4 Claims, 4 Drawing Figures

AURICULAR INSTRUMENT

FIELD OF THE INVENTION

This invention relates to auricular instruments and, more particularly, to an auricular instrument for the therapy of otitis media.

BACKGROUND OF THE INVENTION

Otitis media is a very common childhood infection involving inflammation of the middle ear marked by pain, fever, dizziness and abnormalities of hearing. It frequently requires surgical intervention when antibiotics are not sufficient to bring about recovery. Surgical intervention consists of making a surgical hole in the tympanic membrane, usually performed under general anesthesia. Tubes are placed in the hole for drainage of pus from the afflicted middle ear. The problems raised with the present surgery include: (1) the added risk to the patient with general anesthesia; (2) the necessity of making an appointment for the patient in a hospital for administration of the general anesthesia and surgery at considerable cost to the patient; (3) the usual requirement for the specialist services of an otolaryngologist to perform the operation, again at considerable cost; and (4) the inserted tubes may become blocked or fall out and thus require replacement.

$CO_2$ lasers have been proposed for use in the surgical treatment for diseases such as otitis media. However, such lasers have been difficult to properly aim and are not nearly small enough to be part of a conveniently maneuverable hand-held auricular instrument. Another drawback is that they work by thermal burning, which means that adhesion is formed to the underlying infection and thereby obtains unduly rapid healing in lieu of the moderately progressive healing that results in a successful operation.

SUMMARY OF THE INVENTION

An aim of the invention is to provide an improved device for use in the therapy of otitis media.

Another aim is to provide the foregoing device as a dual-purpose auricular instrument, one purpose being the conventional otoscopic one of looking into the ear of a patient, the other being to form a clean hole in the tympanic membrane of the patient's ear.

Another aim is to provide the foregoing device with a compact Q-switched laser controllable to form with its pulsed output radiation a clean hole in the tympanic membrane of the patient's ear.

Another aim is to provide the foregoing device with a second laser having a CW visible light output for use in illuminating the area in which the clean hole is to be formed, so that the physician looking into the ear of a patient will clearly see the area in the course of the formation of the hole therein.

Another aim is to provide the foregoing device in a form permitting use in any medical practitioner's office at substantially lower cost and risk to the patient than heretofore encountered in surgical therapy of otitis media.

According to the invention, there is provided an auricular instrument for the therapy of otitis media comprising a housing containing a light source and optical means associated therewith for projecting light from the light source onto the outwardly facing surface of a patient's tympanic membrane. The instrument enables visual examination of the tympanic membrane from an eyepiece of the instrument upon insertion of a conically tapered probe of the instrument in the patient's outer ear. The housing further contains a Q-switched laser for providing output pulses of light energy destructive to body tissue, the laser being arranged to use at least part of the optical means in common with the light source such that the laser output pulses will impinge on body tissue at a localized area of the tympanic membrane illuminated by the light source. With this combination of elements, destruction of body tissue results at the localized area impinged upon by the output pulses of light energy from the Q-switched laser. Such tissue destruction can be observed in progress at the viewing end of the auricular instrument with the aid of the illumination of the tympanic membrane provided by the light source.

Preferably, the light source is a low power, second laser for providing a continuous output of visible light energy non-destructive to body tissue.

BRIEF DESCRIPTION OF DRAWINGS

Other aims, features and advantages of the present invention will be apparent from the detailed description of the preferred embodiment thereof in conjunction with the drawings, in which.

DETAILED DESCRIPTION OF THE INVENTION

Figure 1:
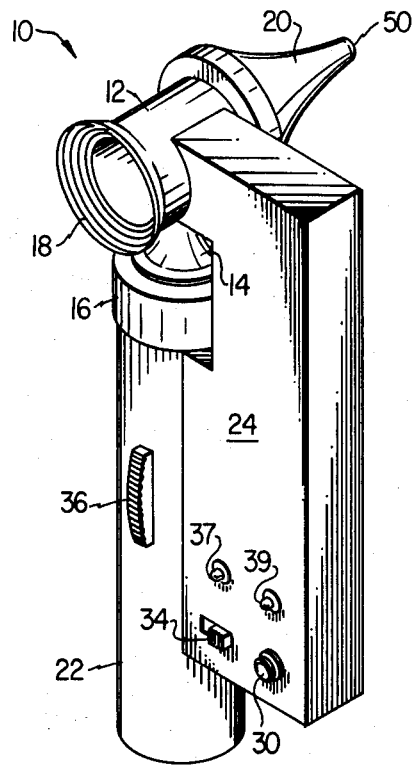
FIG. 1 is an isometric view of an auricular instrument embodying the invention.

Referring now to FIG. 1, the auricular instrument is generally designated with the reference numeral 10 and is shown in its normal orientation for use. A tubular eyepiece 12 of instrument 10 is supported by the top of a downwardly flaring pedestal 14 and horizontally extends diametrically over a cylindrical collar 16 on which pedestal 14 rests. Eyepiece 12 includes a flared viewing end 18 and terminates where it interfaces with the base of a conically tapered hollow probe 20. The small end of probe 20, in use, is inserted by a physician into the outer ear of the patient.

Figure 2:
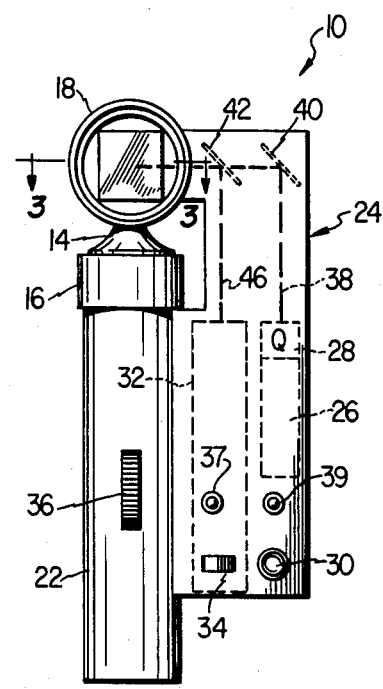
FIG. 2 is a front elevational view of the instrument depicted in FIG. 1, showing in phantom outline representations of the illuminating laser and hole-forming laser, including schematic indications of the respective beam paths of the lasers and the confluence into which they are optically directed.

Coaxially extending downwardly from collar 16 is a cylindrical battery compartment 22 from which operating power for instrument 10 is drawn. A laser compartment 24 has a generally rectangular prismatic shape and is attached along the side of battery compartment 22. Referring to FIG. 2, compartment 24 contains a Neodymium YAG laser 26 equipped with a Q-switch 28 operable through well-known circuitry (not shown) by a pushbutton 30 to selectively produce one or more "giant pulses", depending on how many such pulses or shots are required in a particular situation to form the desired hole in a patient's tympanic membrane. Also disposed within compartment 24, as seen in FIG. 2, is a helium-neon laser 32 which is placed into operation upon manual actuation of a switch 34. Lasers 26 and 32 are placed in a standby condition of readiness by manually actuating a power switch 36 disposed on battery compartment 22. Indicator lights 37 and 39 indicate energization of lasers 26 and 32.

FIG. 2 shows schematically the path 38 of the pulse output of Q-switched laser 26. A reflector 40 redirects path 38 into a horizontal leg for transmission of the pulse output through a reflector 42 associated with CW laser 32 and onwards through an opening 44 (FIGS. 3 and 4) into the interior of eyepiece 12.

Figure 3:
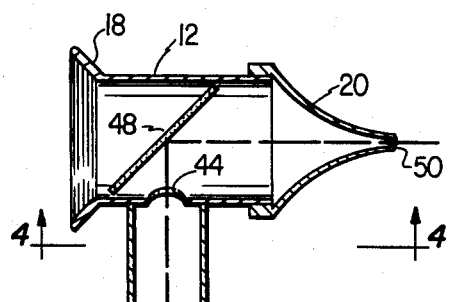
FIG. 3 is a sectional view taken along the lines 3—3 in FIG. 2.
Figure 4:
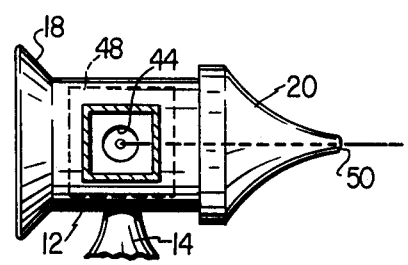
FIG. 4 is a sectional view taken along the lines 4—4 in FIG. 3.

The path 46 of the continuous output of CW laser 32 is also shown schematically in FIG. 2. It, too, is redirected into a horizontal leg, the reflector 42 serving this purpose, and leads the continuous laser output concentrically with the Q-switched laser output horizontally through opening 44 into the interior of eyepiece 12. As shown in FIGS. 3 and 4, both the continuous and pulsed outputs are there intercepted by a reflector 48 angularly disposed with respect to the axis of eyepiece 12. The laser outputs are thus jointly redirected to a path coinciding with the eyepiece axis and pass out the aperture 50 of probe 20 for impingement on a patient's tympanic membrane.

The impinged area of the tympanic membrane is made visible to a physician having his eye against the viewing end 18 of eyepiece 12 by virtue of the continuous laser light reflected back from the impinged area and transmitted through reflector 48 to viewing end 18. The contribution of each "giant pulse" or shot from Q-switched laser 26 to the development of the desired size hole in the tympanic membrane is thus clearly observed by the physician through viewing end 18 of eyepiece 12. Protection of the physician's eyes from the Q-switch radiation would, in practice, be provided by a suitable filter placed in front of the physician's eyes.

The impingement of Q-switched radiation is believed to cause a small explosion in the tissue of a tympanic membrane, which means that one obtains a very clean round hole which is not easily obtained with a surgeon's knife or scalpel. Such a clean hole shows healing such that often tubes will not be required in order to maintain the open hole. Alternatively, tubes may be used when desired. A significant advantage of using the Q-switched laser is that with Q-switching, a plasma is formed. The plasma acts as a shield so that no radiation goes any further into the middle ear. To sum up, use of the invention produces a clean hole, because thermal burning is not used and, instead, a radiation-shielding plasma is formed resulting from a mini-explosion in the membrane tissue caused by the Q-switched radiation.

It will be appreciated that the optical means described herein simply as reflectors 40, 42 and 48, of which 42 and 48 are transmissive as well as reflective, can be mirrors, prisms or any functionally equivalent devices. Moreoever, laser compartment 24 may be either permanently attached to battery compartment 22 or may be removably attached. Rechargeable batteries may be used in compartment 22 with suitable provision for recharging from the mains voltage; or the batteries may be bypassed or eliminated in favor of drawing power directly from the mains.

Although a particular configuration of the invention has been described, it will be understood that the scope of the invention should not be considered limited by the particular embodiment of the illustrated invention, but rather by the appendant claims. For example, laser 26 may be any laser which will Q-switch and emit visible or invisible radiation whose use for the purpose is feasible.

What is claimed is:

1. A handheld, self-contained auricular instrument for the therapy of otitis media, comprising:
    a hollow eyepiece having an ear probe at one end insertable into a patient's ear and having a single axis for enabling the unobstructed viewing of a patient's tympanic membrane;
    a source of visible light harmless to body tissue;
    optical means associated with said light source for directing visible light therefrom along said axis through said ear probe to the patient's tympanic membrane;
    a Q-switched laser for automatically providing output pulses of light explosive to the tympanic membrane, said laser being arranged to use said optical means jointly with said light source to impinge on a target illuminated by said visible light, said output pulses being directed along said axis to said target, whereby said ear probe may be inserted in the outer ear of a patient and said explosive pulses of light used to form a hole in the patient's tympanic membrane while the progress of the hole formation is observed through said eyepiece;
    a first control switch having an "on" state and an "off" state, and located on said handheld instrument for activating said source of visible light; and
    a second control switch on said handheld instrument for activating said laser so that a plurality of said pulses can be output while said switch is operated.

2. The auricular instrument according to claim 1 further including a third switch on said handheld instrument for rendering said first and second switches inactive irrespective of the activation thereof.

3. A method of therapeutically treating otitis media, comprising:
    providing a self-contained instrument having illumination means and pulsed laser means directed along a single axis;
    illuminating a localized area of the patient's tympanic membrane at the side thereof facing the outer ear with visible light along said axis that is non-destructive to body tissue; and
    forming a hole through said tympanic membrane in said localized area thereof by manually controlling the application along said axis of a desired number of energy pulses of Q-switched laser light explosive to the tympanic membrane while utilizing the illumination of said localized area to observe the progress of the hole formation.

4. A method according to claim 3, wherein, following the formation of said hole through the tympanic membrane, a drainage tube is installed in said hole for draining the afflicted middle ear of the patient.

* * * * *